(12) United States Patent
Schreiter et al.

(10) Patent No.: US 12,275,767 B2
(45) Date of Patent: *Apr. 15, 2025

(54) CHEMIGENETIC CALCIUM INDICATORS

(71) Applicant: HOWARD HUGHES MEDICAL INSTITUTE, Chevy Chase, MD (US)

(72) Inventors: Eric R. Schreiter, Leesburg, VA (US); Luke D. Lavis, Ashburn, VA (US); Claire Deo, Heidelberg (DE); Hersh Bhargava, San Francisco, CA (US); Ahmed Abdelfattah, Barrington, RI (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 40 days.

This patent is subject to a terminal disclaimer.

(21) Appl. No.: 18/330,459

(22) Filed: Jun. 7, 2023

(65) Prior Publication Data

US 2023/0416320 A1 Dec. 28, 2023

Related U.S. Application Data

(63) Continuation of application No. 16/768,153, filed as application No. PCT/US2018/068160 on Dec. 31, 2018, now Pat. No. 11,708,397.

(60) Provisional application No. 62/611,666, filed on Dec. 29, 2017.

(51) Int. Cl.
*C07K 14/47* (2006.01)
*A61K 49/00* (2006.01)
(Continued)

(52) U.S. Cl.
CPC ...... *C07K 14/4728* (2013.01); *A61K 49/0004* (2013.01); *A61K 49/0041* (2013.01);
(Continued)

(58) Field of Classification Search
None
See application file for complete search history.

(56) References Cited

U.S. PATENT DOCUMENTS 9,644,007 B2 * 5/2017 Kim ................ G01N 33/5041
9,676,872 B2 6/2017 O'Connell et al.
(Continued)

FOREIGN PATENT DOCUMENTS

WO 2017/070742 A1 5/2017
WO WO-2018219953 A1 * 12/2018 ............ C07K 5/10

OTHER PUBLICATIONS

Meador et al. "Target enzyme recognition by calmodulin: 2.4 A structure of a calmodulin-peptide complex." Science, vol. 257, 5074 (1992): 1251-5. (Year: 1992) (Year: 1992).*

(Continued)

*Primary Examiner* — Rebecca M Giere
*Assistant Examiner* — Alexander Alexandrovic Volkov
(74) *Attorney, Agent, or Firm* — Stites & Harbison, PLLC; Mandy Wilson Decker

(57) ABSTRACT

A chemigenetic calcium indicator and a method of measuring calcium are provided. The chemigenetic calcium indicator includes a calcium-binding protein domain attached to a ligand binding protein domain. The method of measuring calcium includes administering a chemigenetic calcium indicator to a subject and determining changes in fluorescence, the chemigenetic calcium indicator including a ligand binding protein domain having a calcium-binding protein domain and a dye-ligand conjugate attached thereto.

13 Claims, 8 Drawing Sheets

Specification includes a Sequence Listing.

(51) Int. Cl.
*G01N 21/77* (2006.01)
*G01N 33/58* (2006.01)
*G01N 33/84* (2006.01)

(52) U.S. Cl.
CPC ......... *A61K 49/0056* (2013.01); *G01N 21/77* (2013.01); *G01N 33/582* (2013.01); *G01N 33/84* (2013.01); *C07K 2319/20* (2013.01); *C07K 2319/60* (2013.01); *G01N 2021/7786* (2013.01); *G01N 2333/4727* (2013.01)

(56) References Cited

U.S. PATENT DOCUMENTS

2009/0215106 A1* 8/2009 Pribilla ................ G01N 33/542
435/29
2009/0253131 A1 10/2009 Wigdal et al.

OTHER PUBLICATIONS

Kurokawa, et al. "Target-induced conformational adaptation of calmodulin revealed by the crystal structure of a complex with nematode Ca(2+)/calmodulin-dependent kinase kinase peptide." Journal of molecular biology vol. 312, 1 (2001 ): 59-68. (Year: 2001) (Year: 2001).*
Berleant D, White M, Pierce E, Tudoreanu E, Boeszoermenyi A, Shtridelman Y, Macosko JC. The genetic code—more than just a table. Cell Biochem Biophys. 2009;55(2):107-16. (Year: 2009).*
Akerboom et al. "Genetically encoded calcium indicators for multi-color neural activity imaging and combination with optogenetics." Frontiers in molecular neuroscience vol. 6 2. Mar. 4, 2013 (Year: 2013) (Year: 2013).*
Sato et al. "Intracellular Protein-Labeling Probes for Multicolor Single-Molecule Imaging of Immune Receptor-Adaptor Molecular Dynamics," Journal of the American Chemical Society, Nov. 9, 2017 (Nov. 9, 2017), vol. 139, No. 48, pp. 17397-17404.
Best et al. "Protein-specific localization of a rhodamine-based calcium-sensor in living cells," Organic & Biomolecular Chemistry, Apr. 13, 2016 (Apr. 13, 2016), vol. 14, No. 48, pp. 5606-5611.
Sutcliffe et al. "Second-Generation *Drosophila* Chemical Tags: Sensitivity, Versatility, and Speed," Genetics, Feb. 14, 2017 (Feb. 14, 2017), vol. 205, No. 4, pp. 1399-1408.
United States Patent and Trademark Office, International Search Report and Written Opinion issued in corresponding Application No. PCT/US2018/068160, mailed Mar. 18, 2019.

* cited by examiner

CHEMIGENETIC CALCIUM INDICATORS

RELATED APPLICATIONS

This application claims priority from U.S. Provisional Application Ser. No. 62/611,666, filed Dec. 29, 2017, and International Patent Application No. PCT/US2018/068160 filed Dec. 31, 2018, and is a continuation of co-pending U.S. patent application Ser. No. 16/768,153 filed May 29, 2018, the entire disclosures of which are incorporated herein by this reference.

SEQUENCE LISTING

The contents of the electronic sequence listing (Schreiter 18016U2 US18-330459.xml; Size: 31,630 bytes; and Date of Creation: Feb. 11, 2025 is herein incorporated by reference in its entirety.

TECHNICAL FIELD

The presently-disclosed subject matter generally relates to calcium indicators and methods of use thereof. More specifically, the presently-disclosed subject matter relates to chemigenetic calcium indicators and methods of measuring calcium using chemigenetic calcium indicators.

BACKGROUND

Genetically encoded fluorescent calcium indicators (GECI) have become useful reagents for imaging the activity of neurons in the brains of live organisms, in addition to other applications.[1] GECIs use fluorescent protein domains as the fluorescent reporter combined with calcium-binding protein domains in a single polypeptide molecule. Conformational change upon calcium binding alters the fluorescence output of the fluorescent protein domains. However, fluorescent proteins can have limited brightness, photostability, and spectral range, and are generally exceeded by small molecule synthetic fluorophores.

Accordingly, there remains a need for imaging reagents that provide increased brightness, photostability, and/or spectral range.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Provided herein, in some embodiments, is a chemigenetic calcium indicator comprising a calcium-binding protein domain attached to a ligand binding protein domain. In some embodiments, the ligand binding protein domain comprises HaloTag, SNAP-tag, TMP-tag, βLac-tag, CLIP-tag, or a combination thereof. In some embodiments, the ligand binding protein domain comprises a non-covalent capture protein selected from the group comprising a TMP-tag, a biotin-avidin, and a combination thereof. In some embodiments, the calcium binding protein domain comprises calmodulin and a calmodulin binding peptide. In some embodiments, the calcium indicator comprises a DNA sequence according to SEQ ID NO: 1, SEQ ID NO: 3, SEQ ID NO: 5, SEQ ID NO: 7, SEQ ID NO: 9, or SEQ ID NO: 11.

In some embodiments, the chemigenetic calcium indicator further comprises a dye-ligand conjugate attached to the ligand binding protein. In some embodiments, the dye-ligand conjugate comprises a HaloTag ligand conjugated to a fluorescent dye. In some embodiments, the fluorescent dye is selected from the group comprising azetidine-containing Janelia Fluor dyes and rhodamines.

Also provided herein, in some embodiments, is a method of measuring calcium, the method comprising administering a chemigenetic calcium indicator to a subject and determining changes in fluorescence, the chemigenetic calcium indicator comprising a ligand binding protein domain having a calcium-binding protein domain and a dye-ligand conjugate attached thereto. In some embodiments, the ligand binding protein comprises HaloTag and the dye-ligand conjugate comprises a HaloTag ligand conjugated to a fluorescent dye.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIGS. 2A-B show images of nucleotide and amino acid sequences of chemigenetic calcium indicator with sequence features annotated, according to an embodiment of the disclosure. (A) First six lines of the sequences. (B) Last six lines of the sequences.

DESCRIPTION OF EXEMPLARY EMBODIMENTS

Figure 1:
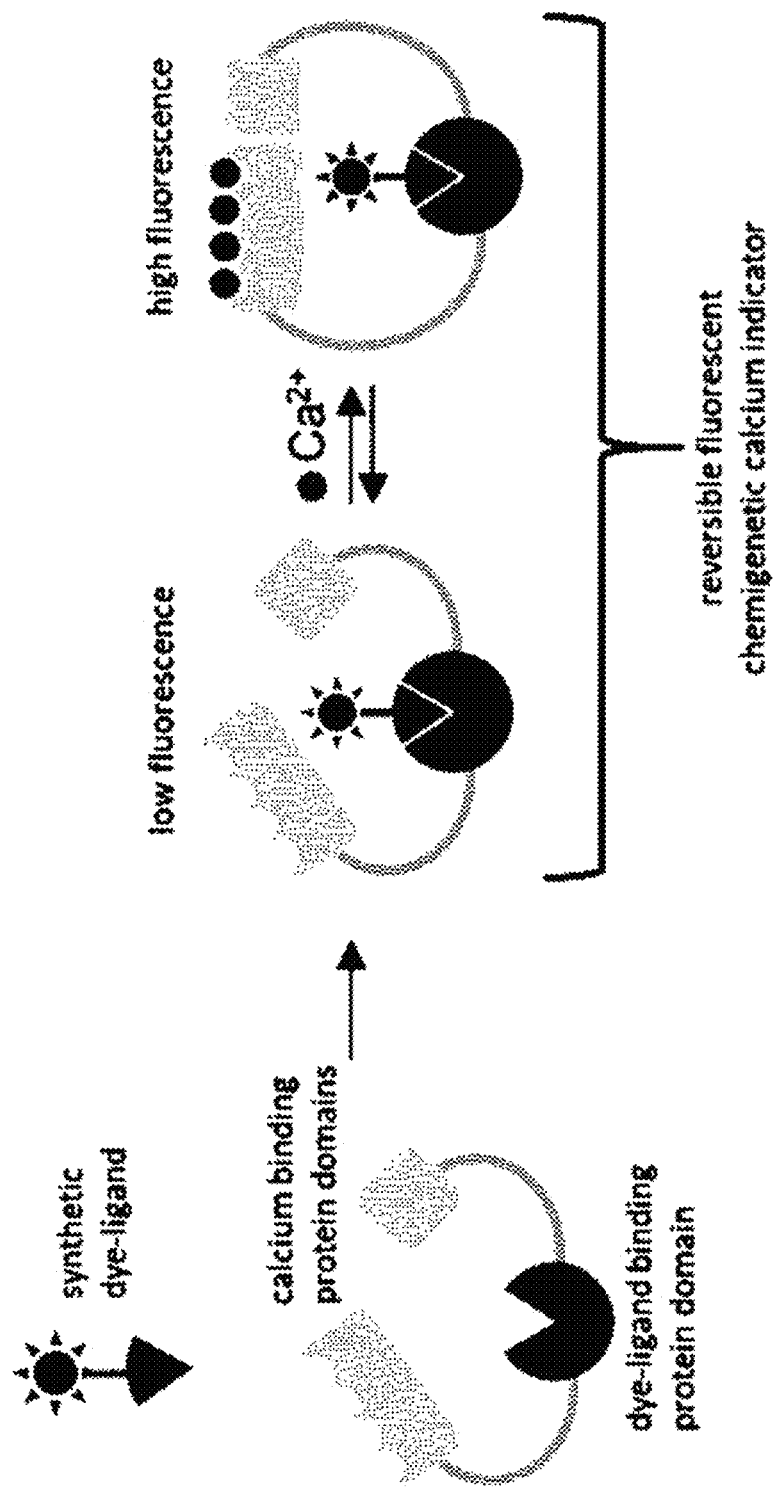
FIG. 1 is a schematic representation of the chemigenetic calcium indicators according to an embodiment of the disclosure.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

The present application can "comprise" (open ended) or "consist essentially of" the components of the present invention as well as other ingredients or elements described herein. As used herein, "comprising" is open ended and means the elements recited, or their equivalent in structure or function, plus any other element or elements which are not recited. The terms "having" and "including" are also to be construed as open ended unless the context suggests otherwise.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter includes calcium indicators and methods of making and using calcium indicators. In some embodiments, the calcium indicators include calcium sensitive fluorophores. For example, in one embodiment, the calcium indicators include a dye-ligand conjugate attached to a ligand binding protein domain (FIG. 1). In another embodiment, attachment of the dye-ligand conjugate to the ligand binding protein domain includes covalent attachment of the dye-ligand conjugate to the ligand binding protein domain. In a further embodiment, the calcium indicators include calcium-binding protein domains attached to the ligand binding protein domain (FIG. 1). This hybrid protein-small molecule including the calcium-binding protein domains attached to the ligand binding protein domain is referred to herein as a "chemigenetic" calcium indicator.

The ligand binding protein domain, or capture protein, includes at least one suitable protein configured to bind the ligand of the dye-ligand conjugate. In some embodiments, the capture protein includes at least one covalent capture protein. For example, in one embodiment, the covalent capture protein includes HaloTag, a modified bacterial haloalkane dehalogenase. In another embodiment, the covalent capture protein includes SNAP-tag. Other suitable covalent capture proteins include, but are not limited to, TMP-tag, βLac-tag, CLIP-tag, or a combination thereof. Additionally or alternatively, the capture protein may include at least one non-covalent capture proteins which capture, or bind, the desired ligand with non-covalent interactions. Suitable non-covalent capture proteins include, but are not limited to, certain TMP-tag, biotin-avidin, or a combination thereof. Although described primarily with regard to a single capture protein, as will be appreciated by those skilled in the art the disclosure is not so limited and may include more than one capture protein, such as multiple covalent capture proteins, multiple non-covalent capture proteins, or a combination of at least one covalent capture protein and at least one non-covalent capture protein.

Figure 2A:
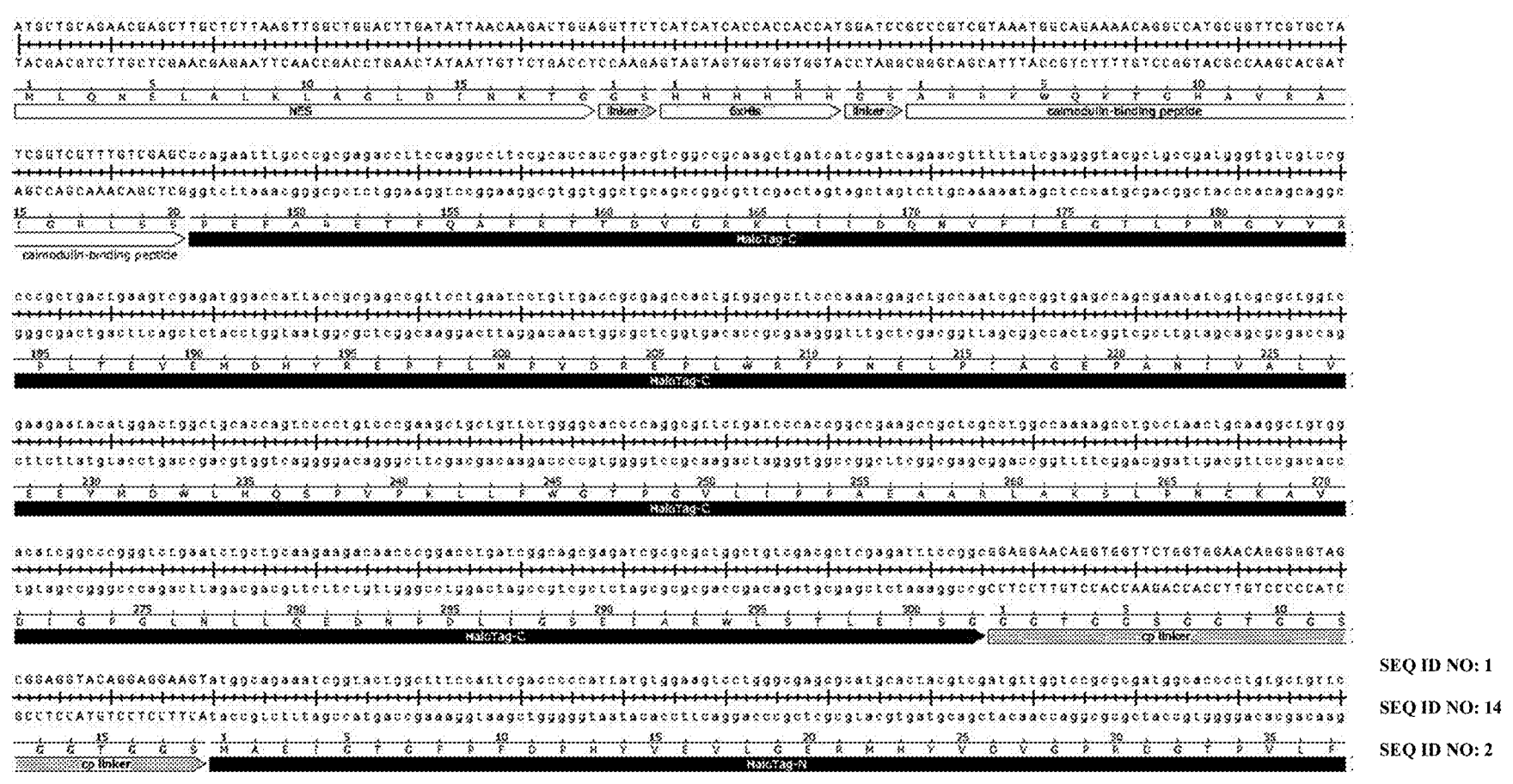
Figure 2B:
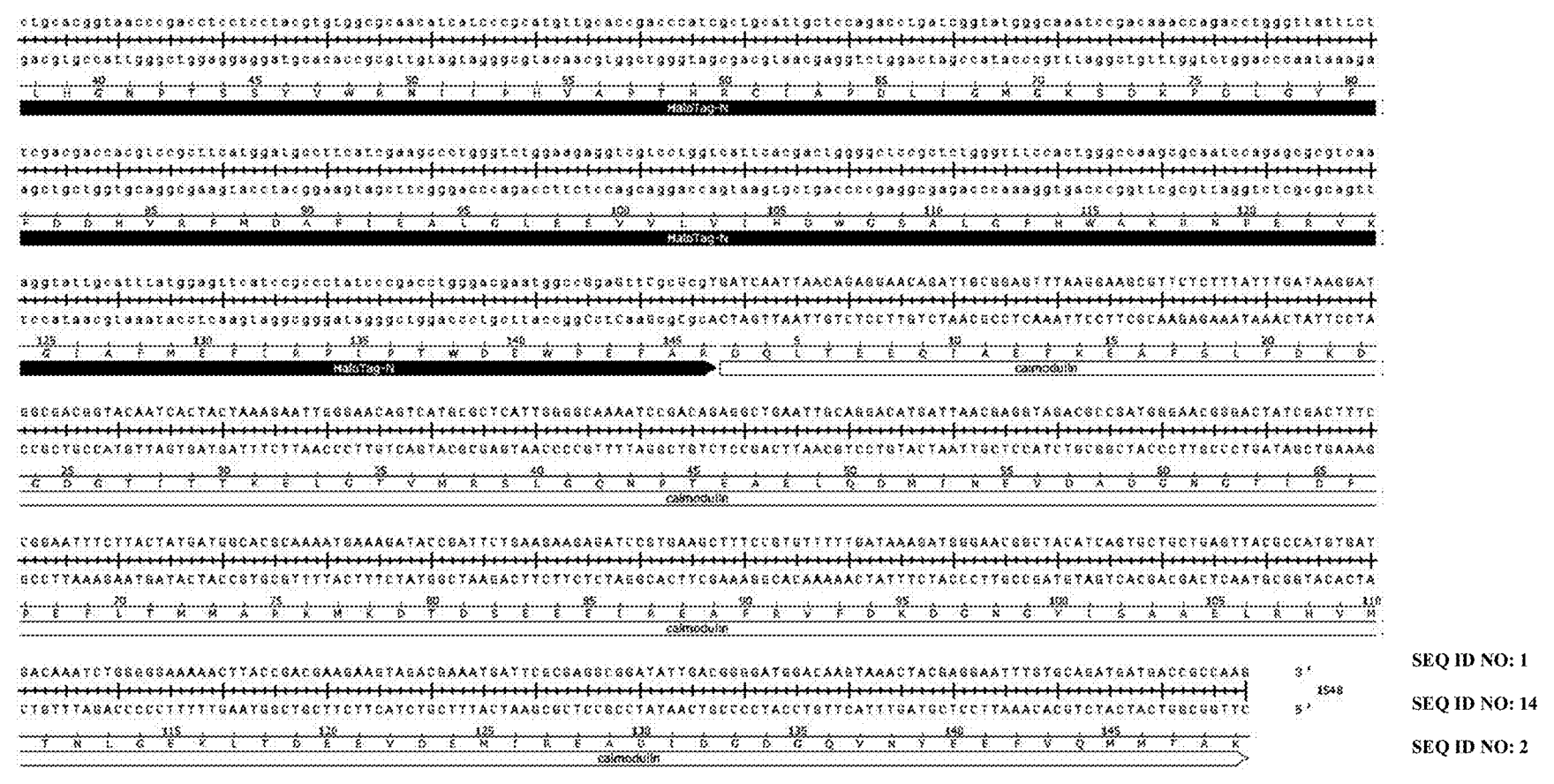

The calcium binding protein domains include any suitable domain or domains for binding calcium and influencing the fluorescence of the dye attached to the ligand binding protein domain. For example, in one embodiment, the calcium-binding protein domains include calmodulin and a calmodulin binding peptide. Other calcium-binding protein domains include, but are not limited to, troponin C, calbindin, calretinin, centrin, any other suitable calcium-binding protein, and/or a combination thereof, along with the associated binding peptide(s) (e.g., calretinin binding peptide for calretinin). As will be appreciated by those skilled in the art, the chemigenetic calcium indicator may include any suitable combination of capture proteins and calcium binding protein domains. FIGS. 2A-B show an example of one such combination (SEQ ID NOs. 1 and 2) that forms a chemigenetic calcium indicator according to one or more of the embodiments disclosed herein. Examples of other such combinations which form the chemigenetic calcium indicator include, but are not limited to, Sv1 (SEQ ID NOs: 3 and 4), A1 (SEQ ID NOs: 5 and 6), C9 (SEQ ID NOs: 7 and 8), C11 (SEQ ID NOs: 9 and 10), and C12 (SEQ ID NOs: 11 and 12).

Additionally or alternatively, in some embodiments, the chemigenetic calcium indicator may include one or more additional domains, such as, but not limited to, a targeting domain, a purification domain, one or more linkers, or a combination thereof. The targeting domain includes any domain for targeting the indicator to a specific location and/or part of a cell. Suitable targeting domains include, but are not limited to, nuclear export signal (NES); nuclear localization signal (NLS); post-synapse targeting domain, such as PSD-95; pre-synapse targeting domain, such as synaptophysin; membrane localization motif, such as prenylation, N-myristoylation, or S-palmitoylation sequences; and/or cellular organelle-targeting motifs, such as a mitochondria-binding domain. The purification domain is for purification and characterization of the indicator, and is not relevant to the function of the indicator itself. Suitable purification domains include, but are not limited to, polyhistamine, chitin-binding protein (CBP)-tag, glutathione-S-transferase (GST)-tag, and/or maltose-binding protein (MBP)-tag. The one or more linkers are for joining various domains within the indicator. Suitable linkers include, but are not limited to, poly-glycine, poly-glycine-serine, poly-glycine-glycine-serine, and/or poly-glycine-glycine-serine-glycine-glycine-threonine (SEQ ID NO: 13). For example, in one embodiment, as illustrated in FIGS. 2A-B, the chemigenetic calcium indicator includes an NES domain, a polyhistadine domain, a poly-Gly-Ser linker attaching the NES domain to the polyhistadine domain, a poly-Gly-Ser linker attaching the polyhistadine domain to the calmodulin-binding peptide, and a poly-Gly-Gly-Ser-Gly-Gly-Thr linker attaching a HaloTag C domain to a HaloTag N domain. Although described above with respect to an indicator including each of the additional domains, as will be appreciated by those skilled in the art the disclosure is not so limited and may include any subset of additional domains (e.g., a targeting domain and one or more linkers) or no additional domains.

Figure 3A:
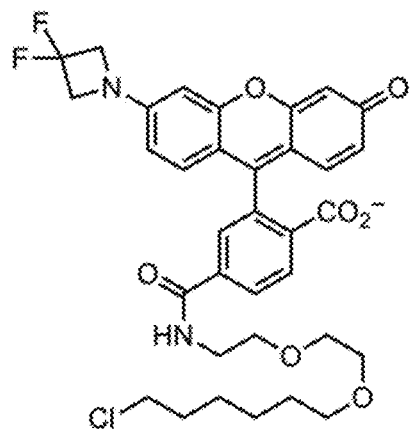
FIGS. 3A-G show chemical structures of various fluorescent dye-ligands according to an embodiment of the disclosure. (A) $JF_{505}$-HaloTag ligand. (B) $JF_{525}$-HaloTag ligand. (C) $JF_{549}$-HaloTag ligand. (D) $JF_{585}$-HaloTag ligand. (E) $JF_{635}$-HaloTag ligand. (F) $JF_{646}$-HaloTag ligand. (G) Tetramethylrhodamine (TMR)-HaloTag ligand.
Figure 3B:
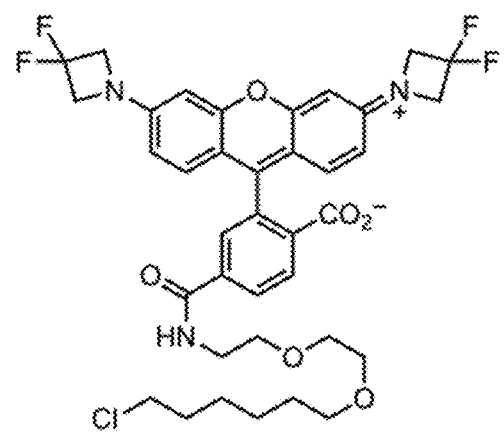
Figure 3C:
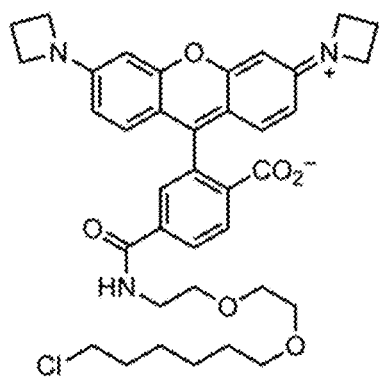
Figure 3D:
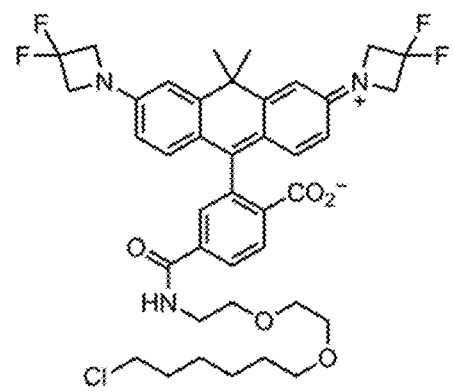
Figure 3E:
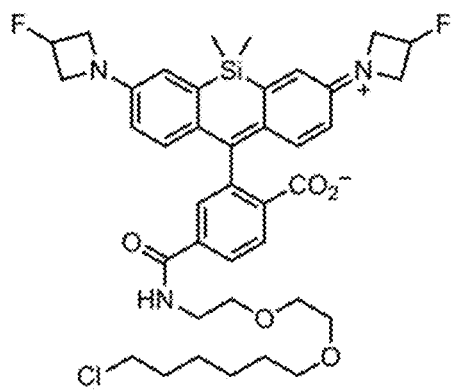
Figure 3F:
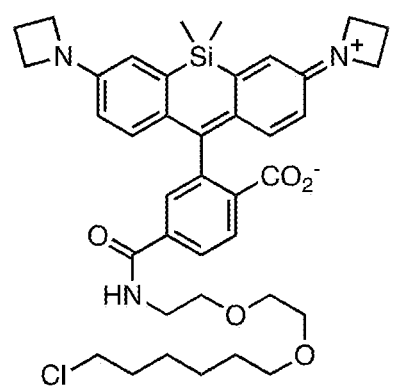
Figure 3G:
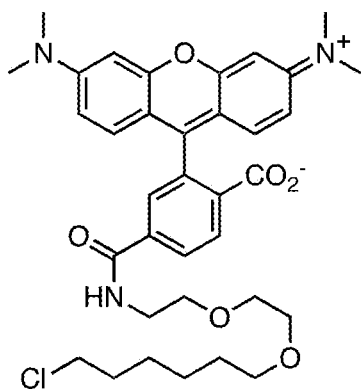

Turning to the dye-ligand conjugate, any suitable dye may be conjugated to any ligand suitable for binding to one or more of the ligand binding protein domains disclosed herein. Suitable dyes include, but are not limited to, fluorescent dyes. In some embodiments, the fluorescent dyes include small-molecule fluorescent dyes such as, but not limited to, one or more fluorophore dyes. In one embodiment, the fluorophore dye includes a fluorophore containing one or more cyclic amine substituents. In another embodiment, the fluorophore dye includes an azetidine-containing rhodamine dye. In a further embodiment, the rhodamine dye includes one or more four-membered azetidine rings in place of the ubiquitous dimethylamino groups of existing fluorophores, forming small, cell-permeable fluorophores having increased brightness and photostability. Such rhodamine dyes include, but are not limited to, Janelia Fluor™$_{505}$, Janelia Fluor™$_{525}$, Janelia Fluor™$_{549}$, Janelia Fluor™$_{585}$, Janelia Fluor™$_{635}$, Janelia Fluor™$_{646}$, and combinations thereof. These dyes are shown in FIGS. 3A-F as attached to a HaloTag ligand. Other suitable dyes include, but are not limited to, rhodamines, such as Tetramethylrhodamine (TMR), which is shown in FIG. 3G as attached to a HaloTag ligand.

As will be appreciated by those skilled in the art, suitable ligands will depend upon the specific ligand binding protein domain being used. Therefore, in some embodiments, the ligand of the dye-ligand conjugate includes any ligand suitable for binding at least one of the ligand binding protein domains disclosed herein. In one embodiment, for example, the ligand includes any suitable ligand for binding HaloTag. Referring to FIGS. 3A-G, in another embodiment, the ligand includes a chloroalkane HaloTag ligand. Other suitable ligands include, but are not limited to, SNAP-tag ligands, TMP-tag ligands, βLac-tag ligands, CLIP-tag ligands, or a combination thereof.

Although one or more of the small molecule synthetic fluorophores disclosed herein is not inherently calcium sensitive, attaching the calcium binding protein domains to the ligand binding protein domain makes such fluorophores calcium sensitive. More specifically, in some embodiments, after binding of the dye-ligand to the ligand binding protein domain, calcium binding to the calcium binding protein domains reversibly changes the fluorescence output of the dye in the attached dye-ligand conjugate.

The hybrid protein-small molecule chemigenetic calcium indicators according to one or more of the embodiments disclosed herein combine the advantages of genetic targetability of proteins with the superior photophysical properties of simple synthetic fluorophores that can be easily delivered to cells. In some embodiments, the calcium indicators disclosed herein provide increased brightness, photostability, and/or spectral range as compared to existing fluorescent proteins. As will be understood by those of ordinary skill in the art, the dyes, ligands, calcium binding protein domains, and capture proteins discussed above are for illustration only and are not intended to limit the scope of the instant disclosure. Accordingly, calcium indicators including any suitable dye, ligand, calcium binding protein domain, and/or capture protein substitute are expressly contemplated herein.

The presently-disclosed subject matter also includes methods of using the calcium indicators. In some embodiments, the methods include measuring changes in calcium levels. For example, in one embodiment, the method includes administering the calcium indicators and measuring changes in fluorescence of the dye by any suitable method. In another embodiment, the changes in fluorescence may be measured through any suitable method such as, but not limited to, observation with a microscope, image capture, video recording, or a combination thereof. In a further embodiment, the changes in fluorescence of the dye may be used to image and/or measure the activity of neurons in live organisms.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Figure 4:
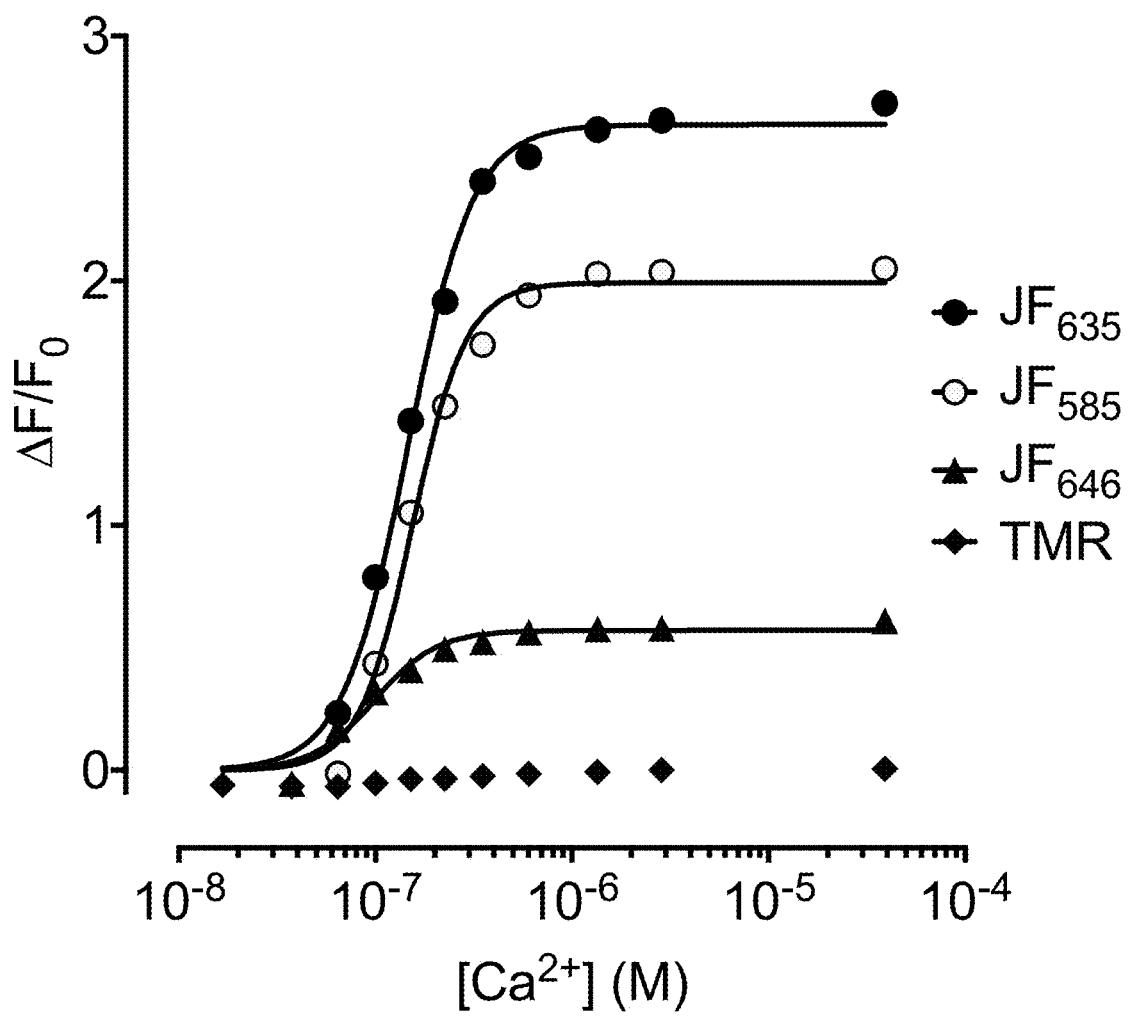
FIG. 4 shows a graph illustrating calcium titrations of chemigenetic calcium indicator protein with $JF_{585}$-HaloTag, $JF_{635}$-HaloTag, $JF_{646}$-HaloTag, and (TMR)-HaloTag dye-ligands bound.
Figure 5A:
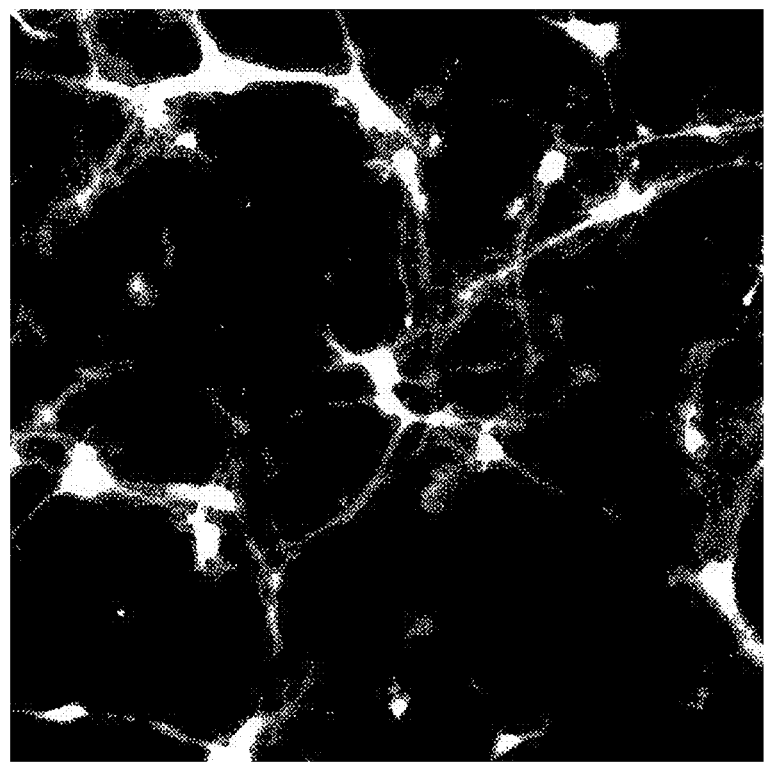
FIGS. 5A-B show graphs and images illustrating fluorescence of rat hippocampal neurons expressing chemigenetic calcium indicator labeled with $JF_{635}$-HaloTag ligand. (A) Fluorescence image of rat hippocampal neurons in culture expressing chemigenetic calcium indicator and labeled with $JF_{635}$-HaloTag ligand. (B) Fluorescence from neurons in (A) in response to action potentials. Action potentials were induced in the neurons with a field electrode during fluorescence imaging. Numbers of action potentials induced appear above each corresponding response in the fluorescence trace (B).
Figure 5B:
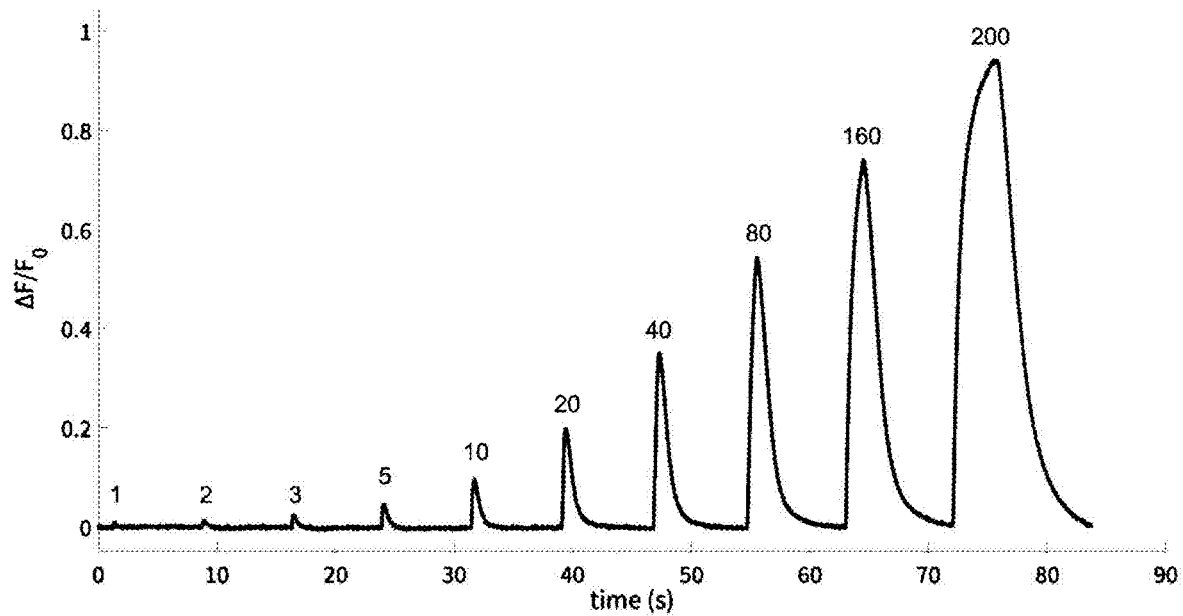

This example describes the formation of a chemigenetic calcium indicator according to an embodiment of the instant disclosure. The chemigenetic calcium indicator was produced by placing the coding sequence of circularly permuted HaloTag between the calcium binding protein calmodulin and a calmodulin binding peptide (SEQ ID NOs: 1 and 2) (FIGS. 2A-B). Incubation of the protein with a fluorescent dye/chloroalkane HaloTag ligand conjugate (FIGS. 3D-G) led to covalent attachment of the fluorescent dye to the protein (FIG. 1). Calcium binding then reversibly changed the fluorescence output of the attached fluorescent dye in both purified protein measurements (FIG. 4) and in rat hippocampal neurons in culture stimulated with a field electrode (FIGS. 5A-B).

Example 2

Figure 6:
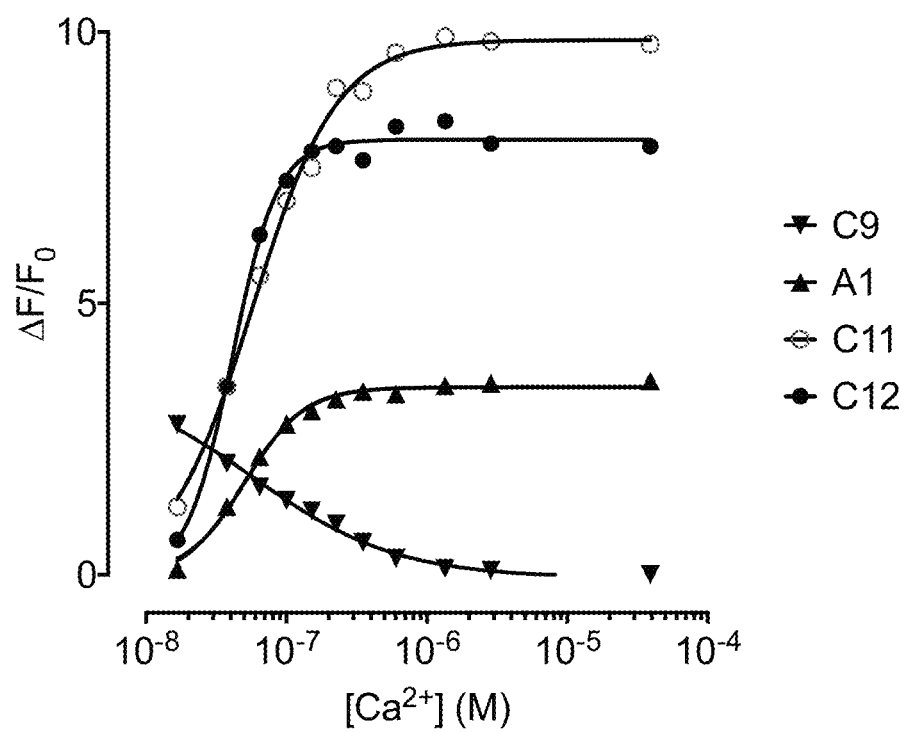
FIG. 6 shows a graph illustrating calcium titrations of chemigenetic calcium indicator proteins bound to $JF_{635}$-HaloTag ligand.

This example compares the fluorescence response of various chemigenetic calcium indicator proteins, including Sv1 (SEQ ID NOs: 3 and 4), A1 (SEQ ID NOs: 5 and 6), C9 (SEQ ID NOs: 7 and 8), C11 (SEQ ID NOs: 9 and 10), and C12 (SEQ ID NOs: 11 and 12), bound to $JF_{635}$-HaloTag ligand. FIG. 6 shows the fluorescence response of the calcium sensor proteins to calcium binding. Table 1 below shows parameters extracted from fits to calcium titrations of chemigenetic calcium indicator proteins bound to $JF_{635}$-HaloTag ligand.

TABLE 1

| Variant | $(\Delta F/F_0)_{max}$ | $K_d$ (nM) | Hill coefficient |
|---|---|---|---|
| Sv1 | 2.6 | 146 | 2.6 |
| A1 | 3.5 | 52 | 2.1 |
| C9 | −3.6 | 58 | 0.9 |
| C11 | 9.9 | 58 | 1.5 |
| C12 | 8.0 | 41 | 2.7 |

As shown in this example, the chemigenetic calcium indicator protein variants have quite different fluorescence responses to binding calcium.

Example 3

Figure 7A:
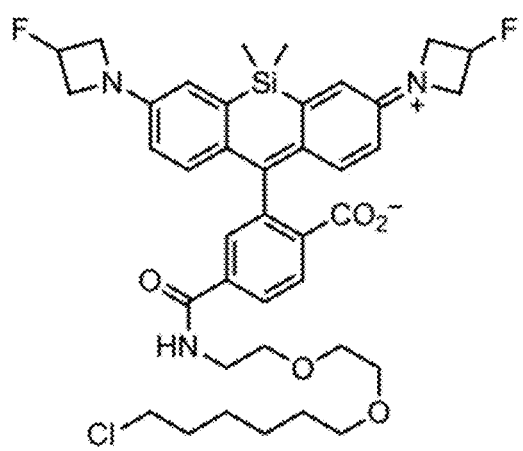
FIGS. 7A-D show graphs and images illustrating various JF-HaloTag ligands and florescence change thereof upon binding calcium. (A) Structure of $JF_{635}$-HaloTag ligand. (B) Derivatives of the azetidine moiety of $JF_{635}$. (C) Fluorescence brightness of $JF_{635}$ derivatives bound to chemigenetic calcium indicator with and without calcium. (D) Magnitude of fluorescence change ($\Delta F/F_0$) of chemigenetic calcium indicator bound to $JF_{635}$ derivatives upon binding calcium.
Figure 7B:
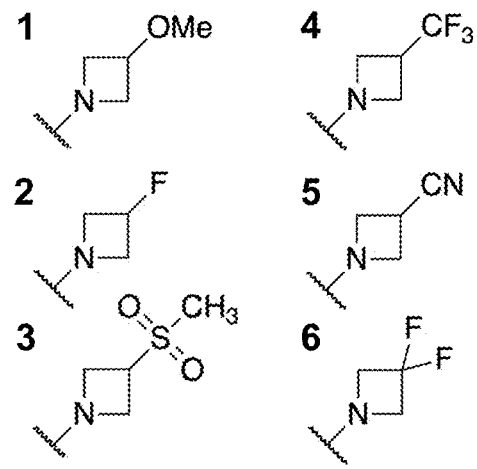

This example describes the formation of various JF-HaloTag ligands and compares the florescence change of calcium indicators including these ligands upon binding calcium. The structure of a $JF_{635}$-HaloTag ligand is shown in FIG. 7A. Through chemical derivatization of the azetidine moiety of $JF_{635}$, the $JF_{635}$-HaloTag ligand derivatives shown in FIG. 7B were produced. Below are $^1$H NMR and HRMS characterizations for these $JF_{635}$-HaloTag ligand derivatives:

1: $^1$H NMR (400 MHz, CDCl$_3$) δ 7.98 (d, J=8.0 Hz, 1H), 7.91 (dd, J=7.9, 1.4 Hz, 1H), 7.69 (s, 1H), 6.84 (s, 1H), 6.76 (d, J=8.7 Hz, 2H), 6.68 (d, J=2.7 Hz, 2H), 6.28 (dd, J=8.7, 2.6 Hz, 2H), 4.35-4.30 (m, 2H), 4.21-4.08 (m, 4H), 3.75-3.72 (m, 4H), 3.66-3.59 (m, 6H), 3.55-3.53 (m, 2H), 3.50 (t, J=6.7 Hz, 2H), 3.38 (t, J=6.7 Hz, 2H), 3.32 (s, 6H), 1.72 (p, J=6.8 Hz, 2H), 1.50 (p, J=6.9 Hz, 2H), 1.45-1.34 (m, 2H), 1.34-1.23 (m, 2H), 0.64 (s, 3H), 0.57 (s, 3H). HRMS (ESI) calculated for C$_{41}$H$_{53}$ClN$_3$O$_7$Si [M+H]$^+$ 762.3341, found 762.3352.

2: $JF_{635}$-HaloTag ligand (published)

3: $^1$H NMR (400 MHz, CDCl$_3$) δ 7.96 (d, J=8.0 Hz, 1H), 7.89 (dd, J=8.0, 1.4 Hz, 1H), 7.67 (d, J=1.3 Hz, 1H), 6.94 (br s, 1H), 6.82 (d, J=8.7 Hz, 2H), 6.69 (d, J=2.6 Hz, 2H), 6.30 (dd, J=8.7, 2.7 Hz, 2H), 4.24-4.18 (m, 8H), 4.16-4.04 (m, 2H), 3.68-3.59 (m, 6H), 3.56-3.54 (m, 2H), 3.49 (t, J=6.6 Hz, 2H), 3.39 (t, J=6.7 Hz, 2H), 2.95 (s, 6H), 1.76-1.66 (m, 2H), 1.51 (p, J=6.9 Hz, 2H), 1.42-1.35 (m, 2H), 1.33-1.22 (m, 2H), 0.64 (s, 3H), 0.56 (s, 3H). HRMS (ESI) calculated for C$_{41}$H$_{53}$ClN$_3$O$_9$S$_2$Si [M+H]$^+$ 858.2681, found 858.2690.

4: $^1$H NMR (400 MHz, CDCl$_3$) δ 8.03-7.97 (m, 1H), 7.90 (dd, J=8.0, 1.4 Hz, 1H), 7.70 (s, 1H), 6.86-6.79 (m, 3H), 6.67 (d, J=2.7 Hz, 2H), 6.29 (dd, J=8.7, 2.7 Hz, 2H), 4.09-4.05 (m, 4H), 3.99-3.94 (m, 4H), 3.66-3.60 (m, 6H), 3.58-3.54 (m, 2H), 3.50 (t, J=6.6 Hz, 2H), 3.42-3.38 (m, 4H), 1.79-1.65 (m, 2H), 1.52 (p, J=6.9 Hz, 2H), 1.45-1.36 (m, 2H), 1.36-1.19 (m, 2H), 0.65 (s, 3H), 0.58 (s, 3H). HRMS (ESI) calculated for C$_{41}$H$_{47}$ClF$_6$N$_3$O$_5$Si [M+H]$^+$ 838.2878, found 838.2891.

5: $^1$H NMR (400 MHz, CDCl$_3$) δ 7.98 (dd, J=8.0, 0.7 Hz, 1H), 7.88 (dd, J=8.0, 1.4 Hz, 1H), 7.70 (s, 1H), 6.84 (d, J=8.7 Hz, 3H), 6.67 (d, J=2.7 Hz, 2H), 6.30 (dd, J=8.7, 2.7 Hz, 2H), 4.22-4.18 (m, 4H), 4.11-4.08 (m, 4H), 3.68-3.54 (m, 10H), 3.50 (t, J=6.6 Hz, 2H), 3.41 (t, J=6.7 Hz, 2H), 1.79-1.67 (m, 2H), 1.52 (p, J=6.9 Hz, 2H), 1.45-1.36 (m, 2H), 1.34-1.21 (m, 2H), 0.66 (s, 3H), 0.58 (s, 3H). HRMS (ESI) calculated for C$_{41}$H$_{47}$ClN$_5$O$_5$Si [M+H]$^+$ 752.3035, found 752.3044.

6: $^1$H NMR (400 MHz, CDCl$_3$) δ 7.99 (d, J=7.9 Hz, 1H), 7.89 (dd, J=8.0, 1.4 Hz, 1H), 7.71 (d, J=1.2 Hz, 1H), 6.87-6.83 (m, 3H), 6.72 (d, J=2.7 Hz, 2H), 6.35 (dd, J=8.7, 2.7 Hz, 2H), 4.23 (t, J=11.7 Hz, 8H), 3.67-3.59 (m, 6H), 3.56-3.54 (m, 2H), 3.50 (t, J=6.6 Hz, 2H), 3.40 (t, J=6.7 Hz, 2H), 1.77-1.68 (m, 2H), 1.57-1.48 (m, 2H), 1.46-1.36 (m, 2H), 1.35-1.22 (m, 2H), 0.67 (s, 3H), 0.59 (s, 3H). HRMS (ESI) calculated for C$_{39}$H$_{45}$ClF$_4$N$_3$O$_5$Si [M+H]$^+$ 774.2753, found 774.2759.

Figure 7C:
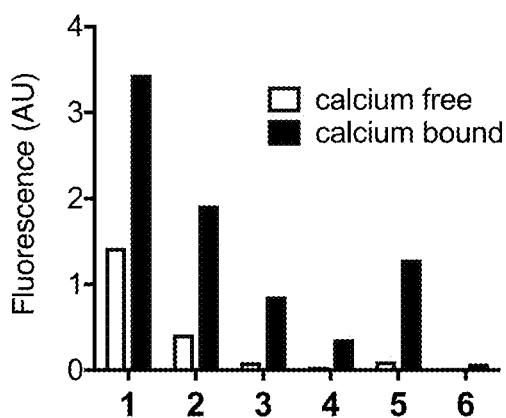
Figure 7D:
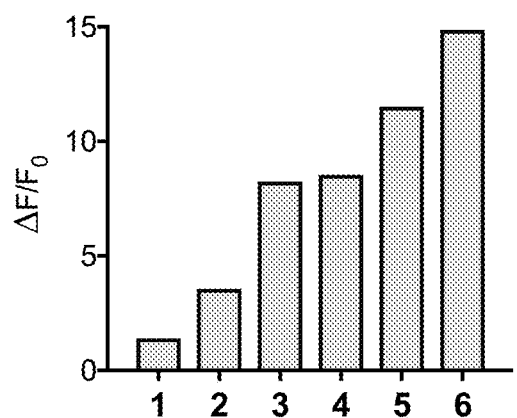

After characterizing these derivatives, the fluorescence brightness thereof was measured when bound to a chemigenetic calcium indicator with and without calcium (FIG. 7C). Additionally, the magnitude of fluorescence change ($\Delta F/F_0$) of the chemigenetic calcium indicator bound to these $JF_{635}$ derivatives was measured upon binding calcium (FIG. 7D). As shown in FIGS. 7C-D, these derivatives formed calcium indicators with variable brightness and fluorescence change when bound to the sensor protein.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lin, M. Z. and M. J. Schnitzer, *Genetically encoded indicators of neuronal activity*. Nat Neurosci, 2016. 19(9): p. 1142-53.
2. Grimm, J. B., et al., *A general method to improve fluorophores for live-cell and single-molecule microscopy*. Nat Methods, 2015. 12(3): p. 244-50, 3 p following 250.
3. Grimm, J. B., et al., *A general method to fine-tune fluorophores for live-cell and in vivo imaging*. Nat Methods, 2017. 14(10): p. 987-994.
4. Los, G. V., et al., *HaloTag: a novel protein labeling technology for cell imaging and protein analysis*. ACS Chem Biol, 2008. 3(6): p. 373-82.

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A nucleic acid, comprising a nucleotide sequence selected from the group consisting of SEQ ID NO: 1, 3, 5, 7, 9, 11, and 14.

2. The nucleic acid of claim 1, comprising the nucleotide sequence of SEQ ID NO: 1.

3. The nucleic acid of claim 1, comprising the nucleotide sequence of SEQ ID NO: 3.

4. The nucleic acid of claim 1, comprising the nucleotide sequence of SEQ ID NO: 5.

5. The nucleic acid of claim 1, comprising the nucleotide sequence of SEQ ID NO: 7.

6. The nucleic acid of claim 1, comprising the nucleotide sequence of SEQ ID NO: 9.

7. The nucleic acid of claim 1, comprising the nucleotide sequence of SEQ ID NO: 11.

8. A chemigenetic calcium indicator, comprising:
(a) a calcium-binding protein domain,
(b) a ligand-binding protein domain attached to the calcium-binding protein domain, and
(c) a fluorescent dye conjugated to a ligand for the ligand-binding protein domain;
wherein the calcium indicator comprises a polypeptide encoded by the nucleic acid of claim 1.

9. The chemigenetic calcium indicator of claim 8, wherein the calcium binding protein domain comprises calmodulin and a calmodulin binding peptide.

10. The chemigenetic calcium indicator of claim 8, wherein the fluorescent dye is selected from the group consisting of azetidine-containing dyes and rhodamines.

11. A method of measuring calcium, the method comprising administering the chemigenetic calcium indicator of claim 8 and determining changes in fluorescence.

12. The method of claim 11, wherein the ligand binding protein comprises a self-labeling protein and the fluorescent dye conjugated to the ligand comprises a ligand for the self-labeling protein conjugated to the fluorescent dye.

13. The nucleic acid of claim 1, comprising the nucleotide sequence of SEQ ID NO: 14.

* * * * *

SEQUENCE LISTING

```
Sequence total quantity: 14
SEQ ID NO: 1            moltype = DNA  length = 1548
FEATURE                 Location/Qualifiers
misc_feature            1..1548
                        note = Synthetic chemigenetic calcium indicator
source                  1..1548
                        mol_type = other DNA
                        organism = synthetic construct
SEQUENCE: 1
atgctgcaga acgagcttgc tcttaagttg gctggacttg atattaacaa gactggaggt   60
tctcatcatc accaccacca tggatccgcc cgtcgtaaat ggcagaaaac aggccatgcg  120
gttcgtgcta tcggtcgttt gtcgagccca gaatttgccc gcgagacctt ccaggccttc  180
cgcaccaccg acgtcggccg caagctgatc atcgatcaga acgtttttat cgagggtacg  240
ctgccgatgg gtgtcgtccg cccgctgact gaagtcgaga tggaccatta ccgcgagccg  300
ttcctgaatc ctgttgaccg cgagccactg tggcgcttcc caaacgagct gccaatcgcc  360
ggtgagccag cgaacatcgt cgcgctggtc gaagaataca tggactggct gcaccagtcc  420
cctgtcccga agctgctgtt ctggggcacc ccaggcgttc tgatcccacc ggccgaagcc  480
gctcgcctgg ccaaaagcct gcctaactgc aaggctgtgg acatcggccc gggtctgaat  540
ctgctgcaag aagacaaccc ggacctgatc ggcagcgaga tcgcgcgctg gctgtcgacg  600
ctcgagattt ccggcggagg aacaggtggt tctggtggaa caggggtag cggaggtaca  660
ggaggaagta tggcagaaat cggtactggc tttccattcg accccatta tgtggaagtc  720
ctgggcgagc gcatgcacta cgtcgatgtt ggtccgcgcg atggcacccc tgtgctgttc  780
ctgcacggta acccgacctc ctcctacgtg tggcgcaaca tcatcccgca tgttgcaccg  840
acccatcgct gcattgctcc agacctgatc ggtatgggca aatccgacaa accagacctg  900
ggttatttct tcgacgacca cgtccgcttc atggatgcct tcatcgaagc cctgggtctg  960
gaagaggtcg tcctggtcat tcacgactgg ggctccgctc tgggtttcca ctgggccaag 1020
cgcaatccag agcgcgtcaa aggtattgca tttatggagt tcatccgccc tatcccgacc 1080
tgggacgaat ggccggagtt cgcgcgtgat caattaacag aggaacagat tgcggagttt 1140
aaggaagcgt tctctttatt tgataaggat ggcgacggta caatcactac taaagaattg 1200
ggaacagtca tgcgctcatt ggggcaaaat ccgacagagg ctgaattgca ggacatgatt 1260
aacgaggtag acgccgatgg gaacgggact atcgactttc cggaatttct tactatgatg 1320
gcacgcaaaa tgaaagatac cgattctgaa gaagagatcc gtgaagcttt ccgtgttttt 1380
gataaagatg ggaacggcta catcagtgct gctgagttac gccatgtgat gacaaatctg 1440
ggggaaaaac ttaccgacga agaagtagac gaaatgatt gcgaggcgga tattgacggg 1500
gatggacaag taaactacga ggaatttgtg cagatgatga ccgccaag              1548

SEQ ID NO: 2            moltype = AA  length = 516
FEATURE                 Location/Qualifiers
REGION                  1..516
                        note = Synthetic chemigenetic calcium indicator
source                  1..516
                        mol_type = protein
                        organism = synthetic construct
SEQUENCE: 2
MLQNELALKL AGLDINKTGG SHHHHHHGSA RRKWQKTGHA VRAIGRLSSP EFARETFQAF   60
RTTDVGRKLI IDQNVFIEGT LPMGVVRPLT EVEMDHYREP FLNPVDREPL WRFPNELPIA  120
GEPANIVALV EEYMDWLHQS PVPKLLFWGT PGVLIPPAEA ARLAKSLPNC KAVDIGPGLN  180
LLQEDNPDLI GSEIARWLST LEISGGGTGG SGGTGGSGGT GGSMAEIGTG FPFDPHYVEV  240
LGERMHYVDV GPRDGTPVLF LHGNPTSSYV WRNIIPHVAP THRCIAPDLI GMGKSDKPDL  300
GYFFDDHVRF MDAFIEALGL EEVVLVIHDW GSALGFHWAK RNPERVKGIA FMEFIRPIPT  360
WDEWPEFARD QLTEEQIAEF KEAFSLFDKD GDGTITTKEL GTVMRSLGQN PTEAELQDMI  420
NEVDADGNGT IDFPEFLTMM ARKMKDTDSE EEIREAFRVF DKDGNGYISA AELRHVMTNL  480
GEKLTDEEVD EMIREADIDG DGQVNYEEFV QMMTAK                           516

SEQ ID NO: 3            moltype = DNA  length = 1461
FEATURE                 Location/Qualifiers
misc_feature            1..1461
                        note = Synthetic chemigenetic calcium indicator
source                  1..1461
```

```
                    mol_type = other DNA
                    organism = synthetic construct
SEQUENCE: 3
gcccgtcgta aatggcagaa aacaggccat gcggttcgtg ctatcggtcg tttgtcgagc    60
ccagaatttg cccgcgagac cttccaggcc ttccgcacca ccgacgtcgg ccgcaagctg   120
atcatcgatc agaacgtttt tatcgagggt acgctgccga tgggtgtcgt ccgcccgctg   180
actgaagtcg agatggacca ttaccgcgag ccgttcctga atcctgttga ccgcgagcca   240
ctgtggcgct tcccaaacga gctgccaatc gccggtgagc cagcgaacat cgtcgcgctg   300
gtcgaagaat acatggactg gctgcaccag tcccctgtcc cgaagctgct gttctggggc   360
accccaggcg ttctgatccc accggccgaa gccgctcgcc tggccaaaag cctgcctaac   420
tgcaaggctg tggacatcgg cccgggtctg aatctgctgc aagaagacaa cccggacctg   480
atcggcagcg agatcgcgcg ctggctgtcg acgctcgaga tttccggcgg aggaacaggt   540
ggttctggtg gaacaggggg tagcggaggt acaggaggaa gtatggcaga aatcggtact   600
ggctttccat tcgacccca ttatgtggaa gtcctgggcg agcgcatgca ctacgtcgat   660
gttggtccgc gcgatggcac ccctgtgctg ttcctgcacg gtaacccgac ctcctcctac   720
gtgtggcgca acatcatccc gcatgttgca ccgacccatc gctgcattgc tccagacctg   780
atcggtatgg gcaaatccga caaaccagac tgggttatt cttcgacga ccacgtccgc   840
ttcatggatg ccttcatcga agccctgggt ctggaagagg tcgtcctggt cattcacgac   900
tggggctccg ctctgggttt ccactgggcc aagcgcaatc cagagcgcgt caaaggtatt   960
gcatttatgg agttcatccg ccctatcccg acctgggacg aatggccgga gttcgcgcgt  1020
gatcaattaa cagaggaaca gattgcggag tttaaggaag cgttctcttt atttgataag  1080
gatggcgacg gtacaatcac tactaaagaa ttgggaacag tcatcgcgtc attggggcaa  1140
aatccgacag aggctgaatt gcaggacatg attaacgagg tagacgccga tgggaacggg  1200
actatcgact tccggaatt tcttactatg atggcacgca aaatgaaaga taccgattct  1260
gaagaagaga tccgtgaagc tttccgtgtt tttgataaag atgggaacgg ctacatcagt  1320
gctgctgagt tacgccatgt gatgacaaat ctggggaaa aacttaccga cgaagaagta  1380
gacgaaatga ttcgcgaggc ggatattgac ggggatggac aagtaaacta cgaggaattt  1440
gtgcagatga tgaccgccaa g                                            1461

SEQ ID NO: 4          moltype = AA  length = 487
FEATURE               Location/Qualifiers
REGION                1..487
                      note = Synthetic chemigenetic calcium indicator
source                1..487
                      mol_type = protein
                      organism = synthetic construct
SEQUENCE: 4
ARRKWQKTGH AVRAIGRLSS PEFARETFQA FRTTDVGRKL IIDQNVFIEG TLPMGVVRPL    60
TEVEMDHYRE PFLNPVDREP LWRFPNELPI AGEPANIVAL VEEYMDWLHQ SPVPKLLFWG   120
TPGVLIPPAE AARLAKSLPN CKAVDIGPGL NLLQEDNPDL IGSEIARWLS TLEISGGGTG   180
GSGGTGGSGG TGGSMAEIGT GFPFDPHYVE VLGERMHYVD VGPRDGTPVL FLHGNPTSSY   240
VWRNIIPHVA PTHRCIAPDL IGMGKSDKPD LGYFFDDHVR FMDAFIEALG LEEVVLIHD   300
WGSALGFHWA KRNPERVKGI AFMEFIRPIP TWDEWPEFAR DQLTEEQIAE FKEAFSLFDK   360
DGDGTITTKE LGTVMRSLGQ NPTEAELQDM INEVDADGNG TIDFPEFLTM MARKMKDTDS   420
EEEIREAFRV FDKDGNGYIS AAELRHVMTN LGEKLTDEEV DEMIREADID GDGQVNYEEF   480
VQMMTAK                                                             487

SEQ ID NO: 5          moltype = DNA  length = 1461
FEATURE               Location/Qualifiers
misc_feature          1..1461
                      note = Synthetic chemigenetic calcium indicator
source                1..1461
                      mol_type = other DNA
                      organism = synthetic construct
SEQUENCE: 5
gcccgtcgta aatggcagaa aacaggccat gcggttcgtg ctatcggtcg tttgtcgagc    60
cctgagtttg cagcggagac cttccaggcc ttccgcacca ccgacgtcgg ccgcaagctg   120
atcatcgatc agaacgtttt tatcgagggt acgctgccga tgggtgtcgt ccgcccgctg   180
actgaagtcg agatggacca ttaccgcgag ccgttcctga atcctgttga ccgcgagcca   240
ctgtggcgct tcccaaacga gctgccaatc gccggtgagc cagcgaacat cgtcgcgctg   300
gtcgaagaat acatggactg gctgcaccag tcccctgtcc cgaagctgct gttctggggc   360
accccaggcg ttctgatccc accggccgaa gccgctcgcc tggccaaaag cctgcctaac   420
tgcaaggctg tggacatcgg cccgggtctg aatctgctgc aagaagacaa cccggacctg   480
atcggcagcg agatcgcgcg ctggctgtcg acgctcgaga tttccggcgg aggaacaggt   540
ggttctggtg gaacaggggg tagcggaggt acaggaggaa gtatggcgga atcggaact   600
ggattcccgt tgatccgca ttatgtgaa gttctgggag agcgcatgca ttatgtggac   660
gttggtcctc gtgatgggac accagtgctg ttccttcacg gcaatccgac atcgtcgtac   720
gtgtggcgta atatcatccc gcacgttgcc cccacgcgtg gctgcattgc cctgactta   780
atggttatgg ggaaaagtga taagcctgat ctgggtact tctttgacga ccacgtacgc   840
ttcatggatg cttttattga agcattgggt ttggaggaag tagttttggt gatccatgat   900
tggggtagtg ctctgggctt ccattgggcc aagcgtaacc cagaacgcgt gaaaggaatt   960
gcctttatgg agttcatccg tccgattcca acatggacg aatggcgaga atttgcacgc  1020
gatcaattaa cagaggaaca gattgcggag tttaaggaag cgttctcttt atttgataag  1080
gatggcgacg gtacaatcac tactaaagaa ttgggaacag tcatcgcgtc attggggcaa  1140
aatccgacag aggctgaatt gcaggacatg attaacgagg tagacgccga tgggaacggg  1200
actatcgact tccggaatt tcttactatg atggcacgca aaatgaaaga taccgattct  1260
gaagaagaga tccgtgaagc tttccgtgtt tttgataaag atgggaacgg ctacatcagt  1320
gctgctgagt tacgccatgt gatgacaaat ctggggaaa aacttaccga cgaagaagta  1380
gacgaaatga ttcgcgaggc ggatattgac ggggatggac aagtaaacta cgaggaattt  1440
```

```
gtgcagatga tgaccgccaa g                                          1461

SEQ ID NO: 6            moltype = AA  length = 487
FEATURE                 Location/Qualifiers
REGION                  1..487
                        note = Synthetic chemigenetic calcium indicator
source                  1..487
                        mol_type = protein
                        organism = synthetic construct
SEQUENCE: 6
ARRKWQKTGH AVRAIGRLSS PEFAAETFQA FRTTDVGRKL IIDQNVFIEG TLPMGVVRPL   60
TEVEMDHYRE PFLNPVDREP LWRFPNELPI AGEPANIVAL VEEYMDWLHQ SPVPKLLFWG  120
TPGVLIPPAE AARLAKSLPN CKAVDIGPGL NLLQEDNPDL IGSEIARWLS TLEISGGGTG  180
GSGGTGGSGG TGGSMAEIGT GFPFDPHYVE VLGERMHYVD VGPRDGTPVL FLHGNPTSSY  240
VWRNIIPHVA PTHRCIAPDL IGMGKSDKPD LGYFFDDHVR FMDAFIEALG LEEVVLVIHD  300
WGSALGFHWA KRNPERVKGI AFMEFIRPIP TWDEWREFAR DQLTEEQIAE FKEAFSLFDK  360
DGDGTITTKE LGTVMRSLGQ NPTEAELQDM INEVDADGNG TIDFPEFLTM MARKMKDTDS  420
EEEIREAFRV FDKDGNGYIS AAELRHVMTN LGEKLTDEEV DEMIREADID GDGQVNYEEF  480
VQMMTAK                                                           487

SEQ ID NO: 7            moltype = DNA  length = 1440
FEATURE                 Location/Qualifiers
misc_feature            1..1440
                        note = Synthetic chemigenetic calcium indicator
source                  1..1440
                        mol_type = other DNA
                        organism = synthetic construct
SEQUENCE: 7
gcccgtcgta aatggcagaa aacaggccat gcggttcgtg ctatcggtcg tttgtcgagc   60
tgggagacct tccaggcctt ccgcaccacc gacgtcggcc gcaagctgat catcgatcag  120
aacgttttta tcgagggtac gctgccgatg gtgtcgtcc gcccgctgac tgaagtcgag  180
atggaccatt accgcgagcc gttcctgaat cctgttgacc gcgagccact gtggcgcttc  240
ccaaacgagc tgccaatcgc cggtgagcca gcgaacatcg tcgcgctggt cgaagaatac  300
atggactggc tgcaccagtc ccctgtcccg aagctgctgt tctggggcac cccaggcgtt  360
ctgatcccac cggccgaagc cgctcgcctg gccaaaagcc tgcctaactg caaggctgtg  420
gacatcggcc cgggtctgaa tctgctgcaa gaagacaacc cggacctgat cggcagcgag  480
atcgcgcgct ggctgtcgac gctcgagatt tccggcggag gaacaggtgg ttctggtgga  540
acaggggta gcggaggtac aggaggaagt atggcggaga tcggaactgg attccgtttt  600
gatccgcatt atgtggaagt tctgggagag cgcatgcatt atgtggacgt tggtcctcgt  660
gatgggacac cagtgctgtt ccttcacggc aatccgacat cgtcgtacgt gtggcgtaat  720
atcatcccgc acgttgcccc cacgcaccgc tgcattgccc ctgacttaat tggtatgggg  780
aaaagtgata agcctgatct ggggtacttc tttgacgacc acgtacgctt catggatgct  840
tttattgaag cattgggttt ggaggaagta gtttttgtga ttcatgattg gggtagtgcn  900
ctggggttcc attgggccaa gcgtaaccca gaacgcgtga aggaattgc tttatggag  960
ttcatccgtc cgattccaac atgggacgaa tggccccgcg atcaattaac agaggaacag 1020
attgcggagt ttaaggaagc gttctcttta tttgataagg atggcgacgg tacaatcact 1080
actaaagaat tgggaacagt catgcgctca ttggggcaaa atccgacaga ggctgaattg 1140
caggacatga ttaacgaggt agacgccgat gggaacggga ctatcgactt ccgaaatttt 1200
cttactatga tggcacgcaa aatgaaagat accgattctg aagaagagat ccgtgaagct 1260
ttccgtgttt ttgataaaga tgggaacggc tacatcagtg ctgctgagtt acgccatgtg 1320
atgacaaatc tggggaaaa acttaccgac gaagaagtag acgaaatgat tcgcgaggcg 1380
gatattgacg gggatggaca agtaaactac gaggaatttg tgcagatgat gaccgccaag 1440

SEQ ID NO: 8            moltype = AA  length = 480
FEATURE                 Location/Qualifiers
REGION                  1..480
                        note = Synthetic chemigenetic calcium indicator
source                  1..480
                        mol_type = protein
                        organism = synthetic construct
SEQUENCE: 8
ARRKWQKTGH AVRAIGRLSS WETFQAFRTT DVGRKLIIDQ NVFIEGTLPM GVVRPLTEVE   60
MDHYREPFLN PVDREPLWRF PNELPIAGEP ANIVALVEEY MDWLHQSPVP KLLFWGTPGV  120
LIPPAEAARL AKSLPNCKAV DIGPGLNLLQ EDNPDLIGSE IARWLSTLEI SGGGTGGSGG  180
TGGSGGTGGS MAEIGTGFPF DPHYVEVLGE RMHYVDVGPR DGTPVLFLHG NPTSSYVWRN  240
IIPHVAPTHR CIAPDLIGMG KSDKPDLGYF FDDHVRFMDA FIEALGLEEV VLVIHDWGSA  300
LGFHWAKRNP ERVKGIAFME FIRPIPTWDE WPRDQLTEEQ IAEFKEAFSL FDKDGDTIT  360
TKELGTVMRS LGQNPTEAEL QDMINEVDAD GNGTIDFPEF LTMMARKMKD TDSEEEIREA  420
FRVFDKDGNG YISAAELRHV MTNLGEKLTD EEVDEMIREA DIDGDGQVNY EEFVQMMTAK  480

SEQ ID NO: 9            moltype = DNA  length = 1470
FEATURE                 Location/Qualifiers
misc_feature            1..1470
                        note = Synthetic chemigenetic calcium indicator
source                  1..1470
                        mol_type = other DNA
                        organism = synthetic construct
SEQUENCE: 9
gtgcgggtta ttcccagact tgatacctg atactcgtga aagcaatggg ccaccgaaaa   60
```

-continued

```
cgattcggta accccttag gcctaaggag accttccagg ccttccgcac caccgacgtc    120
ggccgcaagc tgatcatcga tcagaacgtt tttatcgagg gtacgctgcc gatgggtgtc   180
gtccgcccgc tgactgaagt cgagatggac cattaccgcg agccgttcct gaatcctgtt   240
gaccgcgagc cactgtggcg cttcccaaac gagctgccaa tcgccggtga gccagcgaac   300
atcgtcgcgc tggtcgaaga atacatggac tggctgcacc agtcccctgt cccgaagctg   360
ctgttctggg gcaccccagg cgttctgatc ccaccggccg aagccgctcg cctggccaaa   420
agcctgccta actgcaaggc tgtggacatc ggcccgggtc tgaatctgct gcaagaagac   480
aacccggacc tgatcggcag cgagatcgcg cgctggctgt cgacgctcga gatttccggc   540
ggaggaacag gtggttctgg tggaacaggg ggtagcggag gtacaggagg aagtatggcg   600
gagatcggaa ctggattccc gtttgatccg cattatgtgg aagttctggg agagcgcatg   660
cattatgtgg acgttggtcc tcgtgatggg acaccagtgc tgttccttca cggcaatccg   720
acatcgtcgt acgtgtggcg taatatcatc ccgcacgttg cccccaagca ccgctgcatt   780
gcccctgact taattggtat ggggaaaagt gataagcctg atctggggta cttctttgac   840
gaccacgtac gcttcatgga tgcttttatt gaagcattgg gtttggagga agtagttttg   900
gtgatccatg attggggtag tgctctgggg ttccattggg ccaagcgtaa cccagaacgc   960
gtgaaaggaa ttgcctttat ggagttcatc cgtccgattc aacatgggac gaatggcct   1020
tttgcacgcg atcaattaac agaggaacag attgcgagt taaggaagc gttctcttta   1080
tttgataagg atggcgacgg tacaatcact actaaagaat tgggaacagt catgcgctca   1140
ttggggcaaa atccgacaga ggctgaattg caggacatga ttaacgaggt agacgccgat   1200
gggaacggga ctatcgactt tccggaattt cttactatga tggcacgcaa aatgaaagat   1260
accgattctg aagaagagat ccgtgaagct ttccgtgttt ttgataaaga tgggaacggc   1320
tacatcagtg ctgctgagtt acgccatgtg atgacaaatc tgggggaaaa acttaccgac   1380
gaagaagtag acgaaatgat tcgcgaggcg gatattgacg gggatggaca agtaaactac   1440
gaggaatttg tgcagatgat gaccgccaag                                    1470

SEQ ID NO: 10            moltype = AA    length = 490
FEATURE                  Location/Qualifiers
REGION                   1..490
                         note = Synthetic chemigenetic calcium indicator
source                   1..490
                         mol_type = protein
                         organism = synthetic construct SEQUENCE: 10
VRVIPRLDTL ILVKAMGHRK RFGNPFRPKE TFQAFRTTDV GRKLIIDQNV FIEGTLPMGV    60
VRPLTEVEMD HYREPFLNPV DREPLWRFPN ELPIAGEPAN IVALVEEYMD WLHQSPVPKL   120
LFWGTPGVLI PPAEAARLAK SLPNCKAVDI GPGLNLLQED NPDLIGSEIA RWLSTLEISG   180
GGTGGSGGTG GSGGTGGSMA EIGTGFPFDP HYVEVLGERM HYVDVGPRDG TPVLFLHGNP   240
TSSYVWRNII PHVAPKHRCI APDLIGMGKS DKPDLGYFFD DHVRFMDAFI EALGLEEVVL   300
VIHDWGSALG FHWAKRNPER VKGIAFMEFI RPIPTWDEWP FARDQLTEEQ IAEFKEAFSL   360
FDKDGDGTIT TKELGTVMRS LGQNPTEAEL QDMINEVDAD GNGTIDFPEF LTMMARKMKD   420
TDSEEEIREA FRVFDKDGNG YISAAELRHV MTNLGEKLTD EEVDEMIREA DIDGDGQVNY   480
EEFVQMMTAK                                                          490

SEQ ID NO: 11            moltype = DNA    length = 1464
FEATURE                  Location/Qualifiers
misc_feature             1..1464
                         note = Synthetic chemigenetic calcium indicator
source                   1..1464
                         mol_type = other DNA
                         organism = synthetic construct SEQUENCE: 11
gtgcgggtta ttcccagact tgataccctg atactcgtga aagcaatggg ccaccgaaaa    60
cgattcggta accccttag gcgggagacc ttccaggcct tccgcaccac cgacgtcggc   120
cgcaagctga tcatcgatca gaacgttttt atcgaggta cgctgccgat gggtgtcgtc   180
cgcccgctga agtcgaagat gatggaccat taccgcgagc cgttcctgaa tcctgttgac   240
cgcgagccac tgtggcgctt cccaaacgag ctgccaatcg ccggtgagcc agcgaacatc   300
gtcgcgctgg tcaagaatca catggactgg ctgcaccagt ccctgtccc gaagctgctg   360
ttctggggca ccccaggcgt tctgatccca ccggccgaag ccgctcgcct ggccaaaagc   420
ctgcctaact gcaaggctgt ggacatcggc ccgggtctga atctgctgca agaagacaac   480
ccggacctga tcggcagcga gatcgcgcgc tggctgtcga cgctcgagat ttccggcgga   540
ggaacaggtg gttctggtgg aacaggggt agcggaggta caggaggaag tatggcggag   600
atcggaactg gattcccgtt tgatccgcat tatgtggaag ttctgggaga gcgcatgcat   660
tatgtggacg ttggtcctcg tgatgggaca ccagtgctgt tccttcacgg caatccgaca   720
tcgtcgtacg tgtggcgtaa tatcatcccg cacgttgccc ccaagcaccg ctgcattgcc   780
cctgacttaa ttggtatggg gaaaagtgat aagcctgatc tggggtactt ctttgacgac   840
cacgtacgct tcatggatgc ttttattgaa gcattgggtt tggaggaagt agttttggtg   900
atccatgatt ggggtagtgc tctggggttc catttgggcca agcgtaaccc agaacgcgtg   960
aaaggaattg cctttatgga gttcatccgt ccgattcaa catgggacga atgggccgca  1020
cgcgatcaat taacagagga gcagattgcg gagtttaagg aagcgttctc tttatttgac  1080
aaggatggcg acggtacaat cactactaaa gaattgggaa cagtcatgcg ctcattgggg  1140
caaaatccga cagaggctga attgcaggac atgattaacg gtagacgc gatgggaac   1200
gggactatcg actttccgga atttcttact atgatggcac gcaaaatgaa agataccgat  1260
tctgaagaag agatccgtga agctttccgt gttttgata aagatgggaa cggctacatc  1320
agtgctgctg agttacgcca tgtgatgaca aatctggggg aaaaacttac cgacgaagaa  1380
gtagacgaaa tgattcgcga ggcggatatt gacggggatg gacaagtaaa ctacgaggaa  1440
tttgtgcaga tgatgaccgc caag                                         1464

SEQ ID NO: 12            moltype = AA    length = 488
FEATURE                  Location/Qualifiers
```

```
REGION                  1..488
                        note = Synthetic chemigenetic calcium indicator
source                  1..488
                        mol_type = protein
                        organism = synthetic construct
SEQUENCE: 12
VRVIPRLDTL ILVKAMGHRK RFGNPFRRET FQAFRTTDVG RKLIIDQNVF IEGTLPMGVV    60
RPLTEVEMDH YREPFLNPVD REPLWRFPNE LPIAGEPANI VALVEEYMDW LHQSPVPKLL   120
FWGTPGVLIP PAEAARLAKS LPNCKAVDIG PGLNLLQEDN PDLIGSEIAR WLSTLEISGG   180
GTGGSGGTGG SGGTGGSMAE IGTGFPFDPH YVEVLGERMH YVDVGPRDGT PVLFLHGNPT   240
SSYVWRNIIP HVAPTHRCIA PDLIGMGKSD KPDLGYFFDD HVRFMDAFIE ALGLEEVVLV   300
IHDWGSALGF HWAKRNPERV KGIAFMEFIR PIPTWDEWAA RDQLTEEQIA EFKEAFSLFD   360
KDGDGTITTK ELGTVMRSLG QNPTEAELQD MINEVDADGN GTIDFPEFLT MMARKMKDTD   420
SEEEIREAFR VFDKDGNGYI SAAELRHVMT NLGEKLTDEE VDEMIREADI DGDGQVNYEE   480
FVQMMTAK                                                           488

SEQ ID NO: 13           moltype = AA  length = 6
FEATURE                 Location/Qualifiers
REGION                  1..6
                        note = Linker
source                  1..6
                        mol_type = protein
                        organism = synthetic construct
SEQUENCE: 13
GGSGGT                                                               6

SEQ ID NO: 14           moltype = DNA  length = 1548
FEATURE                 Location/Qualifiers
source                  1..1548
                        mol_type = other DNA
                        organism = synthetic construct
SEQUENCE: 14
cttggcggtc atcatctgca caaattcctc gtagtttact tgtccatccc cgtcaatatc    60
cgcctcgcga atcatttcgt ctacttcttc gtcggtaagt ttttccccca gatttgtcat   120
cacatggcgt aactcagcag cactgatgta gccgttccca tctttatcaa aaacacggaa   180
agcttcacgg atctcttctt cagaatcggt atctttcatt ttgcgtgcca tcatagtaag   240
aaattccgga aagtcgatag tcccgttccc atcggcgtct acctcgttaa tcatgtcctg   300
caattcagcc tctgtcggat tttgcccccaa tgagcgcatg actgttccca attctttagt   360
agtgattgta ccgtcgccat ccttatcaaa taaagagaac gcttccttaa actccgcaat   420
ctgttcctcy gttaattgat cacgcgcgaa ctccggccat tcgtcccagg tcgggatagg   480
gcggatgaac tccattaaat gcaataccit tgacgcgctc tggattgcgc ttggcccagt   540
ggaaacccag agcggagccc cagtcgtgaa tgaccaggac gacctcttcc agacccaggg   600
cttcgatgaa ggcatccatg aagcggacgt ggtcgtcgaa gaaataaccc aggtctggct   660
tgtcggattt gcccataccg atcaggtctg gagcaatgca gcgatggtcg gtgcaacatg   720
cgggatgatg ttgcgccaca cgtaggagga ggtcgggtta ccgtgcagga acagcacagg   780
ggtgccatcg cgcggaccaa catcgacgta gtgcatgcgc tcgcccagga cttccacata   840
atggggtcg aatggaaagc cagtaccgat ttctgccata cttcctcctg tacctccgct   900
accccctgtt ccaccagaac cacctgttcc tccgccggaa atctcgagcg tcgacagcca   960
gcgcgcgatc tcgctgccga tcaggtccgg gttgtcttct tgcagcagat tcagaccccg  1020
gccgatgtcc acagccttgc agttaggcag cttttggcc aggcgagcgg cttcggccgg  1080
tgggatcaga acgcctgggg tgccccagaa cagcagcttc gggacagggg actggtgcag  1140
ccagtccatg tattcttcga ccagcgcgac gatgttcgct ggctcaccgg cgattggcag  1200
ctcgtttggg aagcgccaca gtggctcgcg gtcaacagga ttcaggaacg gctcgcggta  1260
atggtccatc tcgacttcag tcagcgggcg gacgacaccc atcggcagcg taccctcgat  1320
aaaaacgttc tgatcgatga tcagcttgcg gccgacgtcg gtggtgcgga aggcctggaa  1380
ggtctcgcgg gcaaattctg ggctcgacaa acgaccgata gcacgaaccg catggcctgt  1440
tttctgccat ttacgacggg cggatccatg gtggtggtga tgatgagaac ctccagtctt  1500
gttaatatca agtccagcca acttaagagc aagctcgttc tgcagcat                1548
```